United States Patent
Suzuki et al.

(10) Patent No.: US 6,238,704 B1
(45) Date of Patent: *May 29, 2001

(54) SUSTAINED-RELEASE PREPARATION UTILIZING THERMAL CHANGE AND PROCESS FOR THE PRODUCTION THEREOF

(75) Inventors: Yusuke Suzuki; Toshiro Fujii; Hiroshi Tanaka; Satoshi Sakuma; Hitoshi Kadota, all of Osaka (JP)

(73) Assignee: Shionogi & Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/242,730

(22) PCT Filed: Sep. 11, 1997

(86) PCT No.: PCT/JP97/03198

§ 371 Date: Feb. 22, 1999

§ 102(e) Date: Feb. 22, 1999

(87) PCT Pub. No.: WO98/10756

PCT Pub. Date: Mar. 19, 1998

(30) Foreign Application Priority Data

Sep. 13, 1996 (JP) .................................................... 8-242745

(51) Int. Cl.[7] .............................. A61K 9/16; A61K 9/32; A61K 9/22; A61K 9/24

(52) U.S. Cl. ........................... 424/497; 424/482; 424/468; 424/462; 424/472

(58) Field of Search .................................. 424/497, 482, 424/468, 462, 472

(56) References Cited

U.S. PATENT DOCUMENTS

| | | | |
|---|---|---|---|
| 5,395,626 | * | 3/1995 | Kotwal et al. ......................... 424/472 |
| 5,487,901 | * | 1/1996 | Conte et al. .......................... 424/472 |

FOREIGN PATENT DOCUMENTS

| | | | |
|---|---|---|---|
| 55-500709 | 9/1980 | (JP) . | |
| 1-287019 | 11/1989 | (JP) . | |
| 4-368321 | 12/1992 | (JP) . | |
| WO 80/00659 | * 4/1980 | (WO) | ........................................ 9/32 |

* cited by examiner

*Primary Examiner*—Thurman K. Page
*Assistant Examiner*—Amy E Pulliam
(74) *Attorney, Agent, or Firm*—Birch, Stewart, Kolasch & Birch, LLP

(57) ABSTRACT

A sustained-release preparation which can release a highly water-soluble medicinally active ingredient over a long time and a process for the production thereof are provided. The preparation has a sustained-releasing layer formed by heating and melting a layer composed of both an aqueous ethylcellulose latex containing a plasticizer and a wax to miscibilize them.

13 Claims, 1 Drawing Sheet

SUSTAINED-RELEASE PREPARATION UTILIZING THERMAL CHANGE AND PROCESS FOR THE PRODUCTION THEREOF

This application is the national phase under 35 U.S.C. §371 of prior PCT International Application No. PCT/JP97/03198 which has an International filing date of Sep. 11, 1997 which designated the United States of America.

TECHNICAL FIELD

This invention relates to sustained-release preparation which can control release of a highly water-soluble medicinally active ingredient over a long time and process for the production thereof.

BACKGROUND ART

Sustained-releasing methods of highly water-soluble medicinally active ingredients may roughly be classified into the following two types.

The first sustained-releasing method is by forming a matrix (JP-B 60-56122). According to this publication, the sustained-release was attained by the method wherein a water-soluble medicinally ingredient was granulated with hydrophobic substance to form a matrix. However, the control of release over 4 hours or longer is not described in this publication.

The second sustained-releasing method is by film coating (JP-A 63-27424). In this publication, the preparation to be coated with a binder or a film basis by using an organic solvent (the organic solvent method) was described to enable zero-order release over 10 hours or longer.

Though it is easy to control the release by the organic solvent method, its practical application is restricted due to environmental pollution, the remains of organic solvents in the preparation, maintenance of safety, and the like. Therefore, the methods of coating with an aqueous dispersion for sustained-release polymer by using water as a solvent and of coating only with heated and melted wax have recently been attempted.

As an aqueous dispersion for sustained-release polymer, ethylcellulose latex (Aquacoat (trade name), FMC), ethyl acrylate-methyl methacrylate copolymer (Eudragit NE 30D (trade name), Röhm Pharma), aminoalkyl methacrylate (Eudragit RS 30D (trade name), Röhm Pharma), and the like have been developed. However, it is difficult to control the release of highly water-soluble medicinally active ingredients over a long time even by using them. If the ingredient is coated with a very thick controlling layer, zero-order release cannot be achieved. The reasons in the method of controlling the release only with these sustained-release films are exemplified as follows; inconstant crystalinity of formed films, existence of micropores, susceptible to the surface construction of the material to be coated, gradual change of the ability of the releasing control, and the like.

In the method of coating only with heated and melted wax without using any organic solvent (JP-A 5-309314), the control of the initial period release and the sustained-release time are not satisfactory, and the control of release over a long time is difficult by this method.

DISCLOSURE OF INVENTION

In the above situation, the inventors of the present invention have studied sustained-release preparation which can control release of a highly water-soluble medicinally active ingredient over a long time using an aqueous dispersion for sustained-release polymer.

The inventors of the present invention found that the sustained-releasing layer formed by miscibilization of a plasticizer, aqueous ethylcellulose latex, and wax is useful for solving the above problems and accomplished the present invention. The present invention is hereinafter explained in detail.

The present invention relates to sustained-release preparation of a medicinally active ingredient having a sustained-releasing layer formed by miscibilization of a plasticizer, ethylcellulose, and wax.

The present invention further provides the followings; a) the sustained-release preparation wherein an amount of the wax is 20 to 120% by weight to the weight of the ethylcellulose, b) the sustained-release preparation wherein an amount of the plasticizer is 5 to 50% by weight to the weight of the ethylcellulose, c) the sustained-release preparation wherein the sustained-releasing layer is coated with a water soluble polymer, d) the sustained-release preparation wherein the sustained-release preparation of c) is further coated with a layer containing a medicinally active ingredient, e) the sustained-release preparation having a sustained-releasing layer which is formed by heating and melting wax and aqueous ethylcellulose latex containing a plasticizer to miscibilize them, f) a process for preparing sustained-release preparation which comprises miscibilizing a plasticizer, ethylcellulose, and wax in which granules containing a medicinally active gradient are coated with aqueous ethylcellulose latex containing the plasticizer and the wax to form layers, further coated with a water soluble polymer, and then heated, and g) a composition wherein a plasticizer, ethylcellulose, and wax are miscibilized.

When an amount of the wax is 20% by weight or less to the weight of ethylcellulose, the sustained-releasing layer is not formed by miscibilization of the plasticizer, ethylcellulose, and wax with heating. When an amount of the wax is 120% by weight or more to the weight of ethylcellulose, the medicinally active ingredient is slightly released.

When an amount of the plasticizer is 5% by weight or less to the weight of ethylcellulose, the sustained-releasing layer is not formed by miscibilization of the plasticizer, ethylcellulose, and wax with heating. When an amount of the plasticizer is 50% by weight or more to the weight of ethylcellulose, it is difficult to accomplish the sustained-release because the medicinally active ingredient is readily released.

Medicinally active ingredients which are applicable to the present invention ar not restricted to special ones. Highly water soluble medicine such as phenylpropanolamine hydrochloride, potassium chloride, acetaminophen, ephedrine hydrochloride, methylephedrine hydrochloride, caffeine, dihydrocodeine phosphate, oxycodone hydrochloride, water-soluble vitamins such as vitamin B etc., cimetidine, clonazepam, clonidine, isosorbide dinitrate, nitroglycerine, propranolol, scopolamine, morphine, ethenzamide, chlorphenylamine maleate, diphenhydramine hydrochloride, dextromethorphan hydrobromide, noscapine hydrochloride, and the like are especially applicable. The present invention is also applicable to the medical mixture of the above medicine. Especially, phenylpropanolamine hydrochloride is preferable.

The term "plasticizer" herein used means the material that are useful to decrease the modulus of elasticity and the glass transition temperature of high molecular compounds to increase the elasticity of them. For example, triethyl citrate, triacetin, glycerol esters of fatty acids, phthalic acid esters, and the like are exemplified.

The term "aqueous ethylcellulose latex" herein used means the material that ethylcellulose useful as a sustained-release film basis is emulsified and dispersed in water. For example, Aquacoat (trade name, FMC), Surelease (trade name, Colorcon) are exemplified.

The term "wax" herein used means what is known by the person having ordinary skill in the art as useful to control the releasing speed of medicinally active ingredients. For example, higher alcohols such as cetyl alcohol, stearyl alcohol, etc., higher fatty acids such as palmitic acid, stearic acid, etc., glyceroesters such as monoglyceride, triglyceride, etc., fats and oils such as hydrogenated castor oil, hydrogenated beef tallow, etc., wax such as beeswax, carnauba wax, etc., the mixed wax of the above wax at an appropriate ratio, and the like.

Examples of "water soluble polymer" herein used are hydroxypropylcellulose, hydroxypropylmethylcellulose, and the like.

The term "miscibilization" concerning the plasticizer, ethylcellulose, and wax herein used means the phenomenon that the plasticizer accelerates the cohesion and agglutination of ethylcellulose particles and creates a space into which the wax may penetrate. As the result of "miscibilization", the three components come to be a substantially integrated layer to form a homogeneous layer. As described later, "miscibilization" is caused by heating. In the present invention, if the three components come to be a substantially integrated layer and the preparation shows the sustained-release, it is regarded that "miscibilization" has occurred.

BEST MODE FOR CARRYING OUT THE INVENTION

Figure 1:
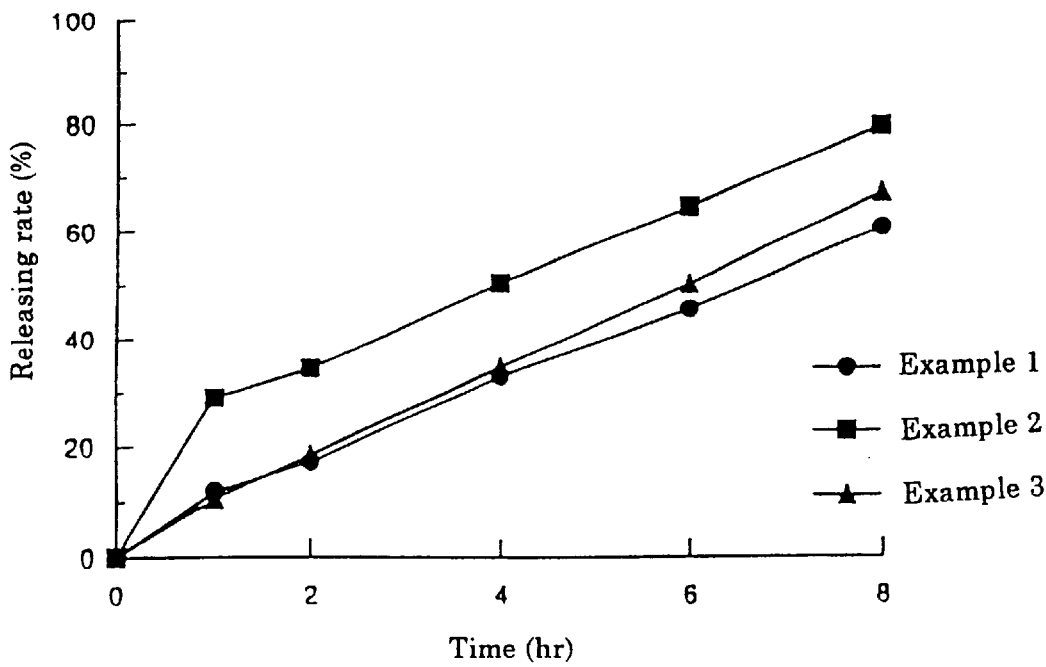
FIG. 1 shows the releasing rate of the medicinally active ingredient with the passage of time concerning each preparation obtained in the Examples 1 to 3.

The sustained-release preparation of the present invention is produced by the method described in the following processes 1) to 5), preferably processes 1) to 6), but is not to be construed to be limited thereto. The sequence of processes 2) and 3) may be inverted, and the processes 2) and 3) may be repeated and be carried out simultaneously. The processes 2) and 3) may be carried out in one step wherein the sustained-release coating solution is prepared by heating the aqueous ethylcellulose latex, the wax, and the plasticizer and the coating solution is used for the coating.

1) Preparation of granules containing a medicinally active ingredient: The granules containing a medicinally active ingredient are not restricted by its shape, size, and the like. Cylindrical granules which are suitable for mass-production or spherical granules of which size is uniform is preferable. As a production method for the former, the method of extruding granulation method in which diluents, binders, and the like which are usually used in the ordinary pharmaceutical production are kneaded and extruded is exemplified. For example, core particles such as sucrose starch spheres, microcrystalline cellulose spheres, etc. are coated with diluents, binders, medicinally active ingredients, and the like using fluidized-bed coater, centrifugal fluidizing granulator, etc. to give spherical granules.

2) Coating with wax: As the method of coating with the wax, the method wherein the granules containing a medicinally active ingredient obtained in 1) are coated with the wax by repeating the spraying of a binder such as water soluble polymer, etc. and the feeding of fine powder wax is exemplified. The method wherein the heated granules are fed and coated with powder wax in accordance with the method of hot-melt coating, the method wherein the heated and melted wax is added or is sprayed to coat, and the like are also exemplified. The amount of the coating varies with solubility of medicinally active ingredients and the desired sustained-release time. Usually, it is possible to achieve the stable controlled release over a long time by coating with the wax of which amount is 5 to 80%, preferably 15 to 55%, by weight to the weight of the granules containing a medicinally active ingredient. An amount of the wax is preferably 20 to 120% by weight to the weight of the ethylcellulose.

3) Coating with aqueous ethylcellulose latex containing the plasticizer: The coating solution is prepared by mixing aqueous ethylcellulose latex with the plasticizer of which amount is 5 to 50%, preferably 10 to 30%, by weight to the weight of the ethylcellulose. The wax coated granules are coated with the coating solution by a fluidized-bed coater, a centrifugal fluidizing granulator, and the like.

4) Coating with a water soluble polymer: The granules obtained in the processes 1) to 3) are coated with a water soluble polymer of which amount is 1 to 5% by weight to the weight of the coated granules by a fluidized-bed coater, a pan coater, a centrifugal fluidizing granulator, and the like. They may further be coated with lubricants, colors, and the like.

5) Forming the sustained-releasing layer by miscibilizing the three component the plasticizer, ethylcellulose, and wax, with heating and melting: The water soluble polymer coated granules are heated at 50° C. to 90° C., at which the wax are usually melted, for 1 to 3 hours by a fluidized-bed coater, a side-vented dryer, and the like. In this process, "miscibilization" occurs between the ethylcellulose layer containing the plasticizer and the wax layer, and the three components come to be an integrated layer This integration was surely confirmed by the electron microscope observation and the sustained-releasing layer was formed.

This miscibilization phenomenon specifically occurs between the ethylcellulose layer containing the plasticizer and the wax layer. The formed layer is able to stabilize the release of highly water-soluble medicine controlled over a long time. Because the miscibilization phenomenon does not occur between the wax and the water soluble polymer coated in the above process, different from hydrophobic polymers such as ethylcellulose, it is considered that the water soluble polymer prevents the wax from oozing out to the surface of the granules.

6) Optionally forming a fast releasing part of a medicinally active ingredient by coating with the medicinally active ingredient on the granules having the sustained-releasing layer obtained in the above processes: The process is carried out by the method wherein the granules having the sustained-releasing layer obtained in the process 5) are coated with the aqueous solution of a medicinally active ingredient, a binder, etc., the powder coating method wherein powder of a medicinally active ingredient is sprayed to them for coating, and the like.

The term "diluent" herein used means the diluents which are used for the ordinary pharmaceutical production, for example, silicic acids such as light anhydrous silicic acid, synthetic aluminum silicate, magnesium aluminometasilicate, etc., inorganic salts such as calcium phosphate, calcium carbonate, calcium sulphate, etc., saccharides such as lactose, sucrose, glucose, mannitol, sorbitol, etc., starches such as corn starch, alpha starch, carboxymethyl starch, etc., celluloses such as microcrystalline cellulose, low substituted hydroxypropylcellulose, etc., Acacia, dextran, pullulan, and the like.

The term "binder" herein used means the binders which are used for the ordinary pharmaceutical production, for example, hydroxypropylcellulose, hydroxypropylmethylcellulose, methylcellulose, polyvinylpyrrolidone, and the like.

The term "lubricant" herein used is exemplified by talc, magnesium stearate, and the like.

The term "colors" herein used is exemplified by lake pigments, and the like.

The sustained-releasing layer of the present invention is not influenced by the pH of the dissolution medium, surface active agents, viscosity, bile acid, enzymes, and the like. Additionally, under any temperature conditions and any humidity conditions, the layer maintains the stable sustained-releasing function. Therefore, this invention provides useful preparation which solves the problems such as compliance and tiresomeness of taking medicine because the release of the medicinally active ingredient is controlled over a long time and enough efficacy of medicine can be obtained by taking it once a day.

As the form of the preparation, capsules wherein the sustained-releasing granules are filled into capsules and tablets which are made by compressing the sustained-releasing granules are applicable.

The following examples and Comparative examples are provided to further illustrate the present invention.

EXAMPLE

Example 1

Using a centrifugal fluidizing granulator (CF granulator, Freund Industrial), 1.36 kg of 32 to 42 meshed sucrose starch spheres as core particles were sprayed with 680 g of 5% hydroxypropylcellulose as a binder and were simultaneously fed and coated with 1.80 kg of phenylpropanolamine hydrochloride as a medicinally active ingredient to give spherical granules. The obtained spherical granules were sprayed with 800 g of aqueous 5% hydroxypropylcellulose solution as a binder and were simultaneously coated with 680 g of crushed hydrogenated castor oil to give 3.91 kg of hydrogenated castor oil-coated granules. Using fluidized-bed coater (Uni-glatt, Okawara), 250 g of the hydrogenated castor oil-coated granules were coated by the method of Waster with the solution which were separately prepared by mixing 5.62 g of triethyl citrate, 13.1 g of fine-ground talc, and 400 g of 15% Aquacoat (Trade name, 旭化成) as aqueous ethylcellulose latex to give 325 g of ethylcellulose-coated granules. The obtained ethylcellulose-coated granules were coated with the water-soluble polymer solution comprising 2.5 g of hydroxypropylcellulose, 3 g of talc, and 98 g of purified water to give water soluble polymer-coated granules. Using the above equipment, the granules were heated and melted at 85° C. for 2 hours with fluidizing and allowed to cool to room temperature to give miscibilized granules.

Example 2

The miscibilized granules (325 g) prepared in Example 1 were charged into a fluidized-bed coater (Wurster-type) and coated with the aqueous solution comprising 28 g of phenylpropanolamine hydrochloride and 5 g of hydroxypropylmethylcellulose by spraying to give miscibilized granules having the fast releasing part.

Example 3

The phenylpropanolamine hydrochloride-coated spherical granules (400 g) prepared midway of Example 1 were charged into a high speed mixer (LFS-GS-1, Fukae Powtec) of which revolution of the agitator was set up to 300 R/M and were coated with 150 g of heated and melted stearyl alcohol at 65° C. In the same way as in Example 1, the obtained wax-coated granules were coated with aqueous ethylcellulose latex and hydroxypropylmethylcellulose. The granules were heated and melted at 80° C. for 2 hours and allowed to cool to room temperature to give miscibilized granules.

Example 4

After mixing 434 g of hydrogenated castor oil, 56.2 g of triethyl citrate, 1.4 kg of purified water, and 131 g of talc, the resulting mixture was heated over 85° C. Using a homomixer (Tokusyu Kika), the mixture was stirred for 20 min at 3000 R/M and 2.0 kg of Aquacoat was added to the mixture. The resulting mixture was stirred for further 10 min and allowed to cool to room temperature to prepare the sustained-release coating solution. The phenylpropanolamine hydrochloride-coated spherical granules (2.5 kg) prepared midway of Example 1 were charged into a fluidized-bed coater (FLO 5, Freund Industrial) and coated with the prepared sustained-release coating solution to give 3.7 kg of sustained-release solution-coated granules. The obtained sustained-release solution-coated granules were coated with 2.5% by weight of the water soluble polymer solution used in Example 1 to the weight of the sustained-release solution-coated granules. The resulting granules were heated and melted at 85° C. for 2 hours and allowed to cool to room temperature to give miscibilized granules.

The obtained granules controlled the release over a long time in the same manner as the granules obtained in Example 1.

Example 5

One kg of phenylpropanolamine hydrochloride as a medicinally active ingredient, 1.27 kg of mannitol, and 0.06 kg of hydrogenated castor oil were charged into 7.5 L Kneader. To the mixture was added 0.3 kg of 7% hydroxypropylcellulose aqueous solution and the resulting mixture was kneaded for 15 min. Using an extruder of which opening size is 0.53 mm, the mixture was granulated and the obtained granules were dried.

The granules (1.5 kg) sized by a power mill to be about 300 to 700 μm were charged into a fluidized-bed coater and were coated with 0.31 kg of fine-ground hydrogenated castor oil while simultaneously spraying with 0.4 kg of 5% hydroxypropylcellulose aqueous solution as a binder.

In the same way as in Example 1, the obtained hydrogenated castor oil-coated granules were coated with Aquacoat by fluidized-bed coater and then with hydroxypropylcellulose and talc. The resulting granules were heated and melted at 85° C. for 2 hours and allowed to cool to room temperature to give sustained-release granules. Additionally, these sustained-release granules were coated with the fast releasing part in the same way as in Example 2 to give miscibilized granules comprising the sustained-releasing and fast releasing parts.

Comparative Example 1

The water-soluble polymer-coated granules prepared midway of Example 1 were only dried by the usual method until the temperature of the granules reaches 50° without melting the wax to give non-miscibilized granules.

Comparative Example 2

Without wax coating, the phenylpropanolamine hydrochloride-coated spherical granules prepared midway of Example 1 were directly coated with Aquacoat solution containing the plasticizer of which composition was the same as in Example 1, heated at 85° C. for 1 hour, and allowed to cool to room temperature to give the granules not including, different from Example 1, the wax.

Comparative Example 3

The hydrogenated castor oil-coated granules (300 g) prepared midway of Example 1 were charged into fluidized-bed coater. The granules were sprayed with the mixture containing 9 g of triethyl citrate and 600 g of 15% aminoalkyl methacrylate (Eudragit RS 30D) instead of Aquacoat to give 390 g of coated granules. In the same way as in Example 1, these granules were coated with hydroxypropylmethylcellulose, heated and melted at 85° C. for 1 hour, and allowed to cool to room temperature to give the same granules as in Example 1 except that aminoalkyl methacrylate was used instead of ethylcellulose.

Figure 2:
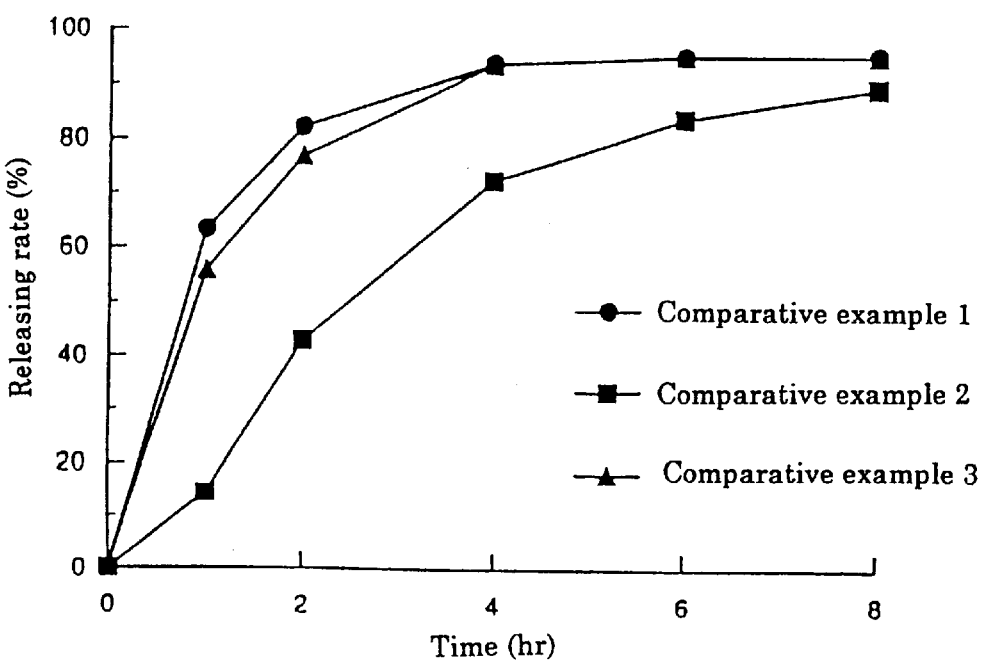
FIG. 2 shows the releasing rate of the medicinally active ingredient with the passage of time concerning each preparation obtained in the Comparative examples 1 to 3.

The results of dissolution tests of the granules obtained in the Examples 1 to 3 and Comparative examples 1 to 3 are shown in FIGS. 1 and 2. The dissolution test was carried out in accordance with the dissolution test method 1 described in Japanese pharmacopeia 12th edition using water as a dissolution medium.

FIG. 1 shows that the miscibilized granules produced in Example 1 are able to control the release of phenylpropanolamine hydrochloride over a long time even though highly water-soluble phenylpropanolamine hydrochloride is used as an active ingredient Because the granules produced in Example 2 have the fast releasing part to be release immediately and the sustained-releasing part, it is realized that efficacy of medicine appears immediately and is maintained for a long time. Additionally, the controlled release of the sustained-releasing part is not degraded by the coating with the fast-releasing part. The granules produced in Example 3 is able to control the release over a long time in a manner similar to those produced in Example 1.

FIG. 2 shows that release of phenylpropanolamine hydrochloride is hardly controlled even though the components of the granules produced in Comparative example 1 are the same as those of Example 1. The granules produced in the Comparative example 2 control the release a little, but sufficient control efficiency is not found. The granules produced in Comparative example 3 hardly control the release of phenylpropanolamine hydrochloride.

Industrial Applicability

The sustained-release preparation which can control the release of a highly water-soluble medicinally active ingredient over a long time and the process for the production thereof are provided.

What is claimed is:

1. A process for preparing a sustained-releasing preparation having a sustained-releasing layer formed by miscibilization of a plasticizer, ethylcellulose, and wax, wherein miscibilization is a phenomenon wherein a plasticizer accelerates cohesion and agglutination of ethylcellulose particles and creates a space into which wax penetrates upon heating, which comprises the following steps:

(1) preparing a granule containing a medicinally active ingredient;

(2) coating said granule with wax in an amount of 20 to 120% by weight to the weight of ethylcellulose;

(3) coating said granule with aqueous ethylcellulose latex containing the plasticizer in an amount of 5 to 50% by weight to the weight of the ethylcellulose;

(4) coating said granule with a water soluble polymer, in an amount of 1 to 5% by weight to the weight of the granule obtained from steps (1) to (3); and (5) forming the sustained-releasing layer by heating the granule at 50° C. to 90° C., wherein the sequence of steps (2) and (3) may be inverted, repeated, and/or carried out simultaneously.

2. The process of claim 1, wherein the wax is selected from the group consisting of cetyl alcohol, stearyl alcohol, palmitic acid, stearic acid, monoglyceride, triglyceride, hydrogenated castor oil, hydrogenated beef tallow, beeswax, carnauba wax, and a mixture of beeswax and carnauba wax.

3. The process of claim 1, wherein the plasticizer is selected from the group consisting of triethyl citrate, triacetin, glycerol esters of fatty acids, and phthalic acid esters.

4. A composition produced by the process of claim 1, wherein a plasticizer, ethylcellulose, and wax are miscibilized.

5. A sustained-release preparation of a medicinally act ingredient produced by the Process of claim 1, which has a sustained-releasing layer formed by miscibilization of a plasticizer, ethylcellulose, and wax, wherein miscibilization is a phenomenon wherein a plasticizer accelerates cohesion and agglutination of ethylcellulose particles and creates a space into which wax penetrates upon heating.

6. The sustained-release preparation of claim 5 wherein an amount of the wax is 20 to 120% by weight to the weight of the ethylcellulose.

7. The sustained-release preparation of claim 5 wherein an amount of the plasticizer is 5 to 50% by weight to the weight of the ethylcellulose.

8. The sustained-release preparation of claim 5, wherein the sustained-releasing layer is coated with a water soluble polymer that prevents the wax from oozing out to a surface of the preparation during miscibilization.

9. The sustained-release preparation of claim 4 wherein the preparation is further coated with a layer containing a medicinally active ingredient.

10. The sustained-release preparation of claim 5 which has a sustained-releasing layer formed by heating and melting wax and aqueous ethylcellulose latex containing a plasticizer to miscibilize them.

11. The sustained-release preparation of claim 5, wherein the sustained-releasing layer controls the release of a highly water-soluble medicinally active ingredient over time.

12. The sustained-release preparation of claim 5, wherein the sustained-releasing layer is coated with a water soluble polymer that prevents the wax from oozing out to a surface of the preparation during miscibilization, in an amount of 1 to 5% by weight to the weight of the coated granules.

13. A method for controlling the release of a highly water-soluble medicinally active ingredient over time which comprises surrounding said medicinally active ingredient with a sustained-releasing layer formed by the process of claim 1, wherein miscibilization is a phenomenon wherein a plasticizer accelerates cohesion and agglutination of ethylcellulose particles and creates a space into which wax penetrates upon heating.

* * * * *